(12) United States Patent
Gross et al.

(10) Patent No.: US 8,504,209 B2
(45) Date of Patent: Aug. 6, 2013

(54) CONTROLLING A DEVICE THAT GENERATES VIBRATIONS IN A COMPUTER SYSTEM

(75) Inventors: Kenny C. Gross, San Diego, CA (US); Aleksey M. Urmanov, San Diego, CA (US); Kalyanaraman Vaidyanathan, San Diego, CA (US)

(73) Assignee: Oracle America, Inc., Redwood Shores, CA (US)

( * ) Notice: Subject to any disclaimer, the term of this patent is extended or adjusted under 35 U.S.C. 154(b) by 815 days.

(21) Appl. No.: 12/220,952

(22) Filed: Jul. 29, 2008

(65) Prior Publication Data

US 2010/0024555 A1 Feb. 4, 2010

(51) Int. Cl.
*G05B 15/00* (2006.01)
*G01N 29/12* (2006.01)

(52) U.S. Cl.
USPC ............ 700/280; 73/579; 73/570; 73/658; 324/312; 324/166; 702/75; 702/76; 702/77; 361/679.34; 720/679; 700/300; 713/100

(58) Field of Classification Search
USPC ....... 700/280; 720/679; 324/312; 702/75–77; 361/679.34; 73/579
See application file for complete search history.

(56) References Cited

U.S. PATENT DOCUMENTS

| 5,203,178 | A * | 4/1993 | Shyu ............................ 62/180 |
| 5,631,427 | A * | 5/1997 | Bridges ........................ 73/658 |
| 6,220,045 | B1 * | 4/2001 | Kim .......................... 62/228.4 |
| 6,601,168 | B1 * | 7/2003 | Stancil et al. ................. 713/100 |
| 7,075,261 | B2 * | 7/2006 | Burstein ................... 318/400.11 |
| 7,193,799 | B2 * | 3/2007 | Chung ........................... 360/46 |
| 7,487,401 | B2 * | 2/2009 | Urmanov et al. ............... 714/42 |
| 7,565,226 | B1 * | 7/2009 | Cooley et al. ................ 700/280 |
| 7,711,452 | B2 * | 5/2010 | Konstadinidis et al. ...... 700/280 |
| 7,761,244 | B2 * | 7/2010 | Gross et al. .................... 702/34 |
| 7,877,167 | B1 * | 1/2011 | Patel et al. ................... 700/280 |
| 2002/0123860 | A1 * | 9/2002 | Fioravanti et al. ............ 702/182 |
| 2004/0165406 | A1 * | 8/2004 | Gauthier et al. ................ 363/39 |
| 2004/0239279 | A1 * | 12/2004 | Komiya et al. ............... 318/606 |
| 2008/0310967 | A1 * | 12/2008 | Franz et al. ..................... 417/32 |
| 2009/0067080 | A1 * | 3/2009 | Gross et al. .................... 360/71 |
| 2009/0159581 | A1 * | 6/2009 | Sommerfeld ................ 219/133 |

FOREIGN PATENT DOCUMENTS

JP 59-211797 * 11/1984

* cited by examiner

*Primary Examiner* — Kavita Padmanabhan
*Assistant Examiner* — Olvin Lopez Alvarez
(74) *Attorney, Agent, or Firm* — Park, Vaughan, Fleming & Dowler, LLP

(57) ABSTRACT

Some embodiments of the present invention provide a system that controls a device that generates vibrations in a computer system. During operation, a critical vibration frequency is determined for the computer system. Next, a keep-out zone is generated based on the critical vibration frequency, wherein the keep-out zone specifies a range of frequencies to be avoided. Then, the device is controlled based on the keep-out zone to reduce vibrations generated by the device in the keep-out zone.

19 Claims, 2 Drawing Sheets

CONTROLLING A DEVICE THAT GENERATES VIBRATIONS IN A COMPUTER SYSTEM

The patent or application file contains at least one drawing executed in color. Copies of this patent or patent application publication with color drawing(s) will be provided by the Office upon request and payment of the necessary fee.

BACKGROUND

1. Field

The present invention generally relates to techniques for operating a computer system. More specifically, the present invention relates to a method and apparatus that controls a device that generates vibrations in a computer system.

2. Related Art

Many new computer systems include powerful processors that require more powerful fans to cool them. These more powerful fans can increase the vibrations generated in the computer system and lead to performance problems for components in the computer system. For example, many new higher density disk drives have smaller track sizes and tighter tolerances to increase their storage capacity. However, smaller track sizes and tighter tolerances makes such disk drives potentially more sensitive to vibrations during operation of the computer system.

Hence, what is needed is a method and apparatus that controls a device that generates vibrations in a computer system, without the above-described problems.

SUMMARY

Some embodiments of the present invention provide a system that controls a device that generates vibrations in a computer system. During operation, a critical vibration frequency is determined for the computer system. Next, a keep-out zone is generated based on the critical vibration frequency, wherein the keep-out zone specifies a range of frequencies to be avoided. Then, the device is controlled based on the keep-out zone to reduce vibrations generated by the device in the keep-out zone.

In some embodiments, determining the critical vibration frequency includes monitoring a computer system component performance parameter while the computer system is vibrating in a frequency range.

In some embodiments, determining the critical vibration frequency includes determining the critical vibration frequency based on monitoring a performance parameter of the computer system during operation of the computer system and monitoring a vibration frequency of the computer system during operation of the computer system.

In some embodiments, the computer system is vibrated in the frequency range using a vibration-generation mechanism located inside the computer system.

In some embodiments, determining the critical vibration frequency for the computer system includes determining a critical vibration frequency for each computer system component in a set of computer system components in the computer system.

Some embodiments additionally include generating a library of critical vibration frequencies for the computer system based on the critical vibration frequency for each computer system component in the set of computer system components, wherein generating the keep-out zone includes generating the keep-out zone based on critical vibration frequencies in the library of critical vibration frequencies.

In some embodiments, determining the critical vibration frequency includes determining the critical vibration frequency based on monitoring a performance parameter of the computer system during operation of the computer system.

In some embodiments, controlling the device based on the keep-out zone includes controlling the device to limit a duration of vibrations generated by the device at the critical frequency.

In some embodiments, the device includes at least one of a fan and a disk drive.

DETAILED DESCRIPTION

The following description is presented to enable any person skilled in the art to make and use the disclosed embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present description. Thus, the present description is not intended to be limited to the embodiments shown, but is to be accorded the widest scope consistent with the principles and features disclosed herein.

The data structures and code described in this detailed description are typically stored on a computer-readable storage medium, which may be any device or medium that can store code and/or data for use by a computer system. This includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media.

Figure 1:
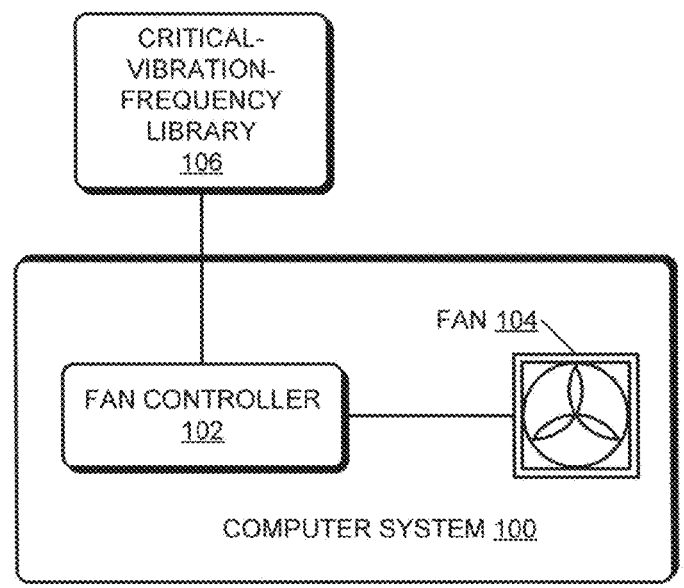
FIG. 1 represents a system that controls a device that generates vibrations in a computer system in accordance with some embodiments of the present invention.

FIG. 1 represents a system that controls a device that generates vibrations in a computer system in accordance with some embodiments of the present invention. Computer system 100 includes fan controller 102 coupled to fan 104. Critical-vibration-frequency library 106 is coupled to fan controller 102.

Computer system 100 can include but is not limited to a server, a server blade, a datacenter server, an enterprise computer, a field-replaceable unit (FRU) that includes a processor, or any other computation system that includes one or more processors and one or more cores in each processor.

Fan controller 102 can be any controller that can control the revolutions per minute (RPMs) or speed of fan 104. Fan controller 102 can be implemented in any combination of hardware and software. In some embodiments, fan controller 102 operates on a processor in computer system 100. In some embodiments, fan controller 102 operates on one or more service processors. In still other embodiments, fan controller 102 operates on a processor outside of computer system 100.

Fan 104 can include any type of fan that can be used to cool computer system 100 or any portion of computer system 100, and can include but is not limited to a main cooling fan, a power supply unit fan, a blower, or a processor cooling fan. Fan 104 can be implemented in any technology. In some embodiments, fan 104 generates vibrations related to the RPMs of fan 104.

Critical-vibration-frequency library 106 can include any mechanism that can store one or more critical frequencies of computer system 100 and transmit them to fan controller 102. Critical-vibration-frequency library 106 can be implemented in any combination of hardware and software. In some embodiments, critical-vibration-frequency library 106 operates on a processor in computer system 100. In other embodiments, critical-vibration-frequency library 106 operates on one or more service processors. In other embodiments, critical-vibration-frequency library 106 operates on a separate computer system. In some embodiments, critical-vibration-frequency library 106 is integrated into fan controller 102. In some embodiments, critical-vibration-frequency library 106 includes a connection to a network such as the internet to send and receive critical vibration frequency information.

Some embodiments of the present invention operate as follows. Critical vibration frequencies of computer system 100 are stored in critical-vibration-frequency library 106. It is noted that critical vibration frequencies of computer system 100 can include but are not limited to critical vibration frequencies of a computer system component in computer system 100, which may include critical frequencies of the computer system component when integrated into computer system 100 and/or when not integrated into computer system 100. In some embodiments, critical vibration frequencies include but are not limited to: resonant frequencies of computer system 100 and/or any computer system component in computer system 100; any other vibration frequencies that cause an alteration or degradation in the performance or behavior of computer system 100 and/or any computer system component in computer system 100; or harmonic frequencies of critical frequencies.

Critical vibration frequencies of computer system 100 can be identified using any method or apparatus. In some embodiments, a performance parameter of computer system 100 is monitored as computer system 100 is vibrated in a frequency range. Critical vibration frequencies of computer system 100 are then identified based on changes in performance parameters as the vibration frequency is changed. In some embodiments, performance parameters include but are not limited to performance parameters as set forth in U.S. Pat. No. 7,020,802, entitled "Method and Apparatus for Monitoring and Recording Computer System Performance Parameters," by Kenny C. Gross and Larry G. Votta, Jr., issued on 28 Mar. 2006, which is hereby fully incorporated by reference. In some embodiments, the critical vibration frequencies of computer system 100 are determined at regular intervals, when the configuration of computer system 100 is changed, and/or when the location of computer system 100 is changed.

In some embodiments, critical vibration frequencies of computer system 100 are determined during operation of computer system 100 by monitoring performance parameters of computer system 100. A change in or degradation of a performance parameter is used to indicate the presence of a critical frequency. For example, a critical vibration frequency of a hard disk drive may be indicated by a change in a performance parameter such as a read rate or write rate for the hard disk drive as the speed of fan 104 is changed. The speed of fan 104 can then be used to identify the critical vibration frequency.

In some embodiments, critical vibration frequencies of computer system 100 can include but are not limited to structural resonances of computer system 100. In some embodiments, critical vibration frequencies of computer system 100 and/or any computer system component in computer system 100 are determined using an apparatus or method described in U.S. Pat. No. 7,890,278, entitled "Characterizing the Response of a Device in a Computer System to Vibration over a Frequency Range," by Dan Vacar, Anton A. Bougaev, David K. McElfresh, and Kenny C. Gross, filed 28 Jul. 2008, which is hereby fully incorporated by reference; and/or a U.S. patent application entitled "Built-in Swept-Sine Testing for a Computer System to Assure Vibrational Integrity," by Kenny C. Gross, and Aleksey M. Urmanov, application Ser. No. 11/787,782, filed 17 Apr. 2007, which is hereby fully incorporated by reference.

In some embodiments, critical-vibration-frequency library 106 generates keep-out zones based on the critical vibration frequencies. In some embodiments, a keep-out zone is a range of vibration frequencies that includes the critical vibration frequency and has a frequency width based on measurements related to determining the critical vibration frequency. For example, in some embodiments, if a resonance frequency of a hard disk drive is determined based on vibration testing of the hard disk drive, the width of the keep-out zone based on the resonant frequency of the hard disk drive can be generated based on the vibration frequencies higher and lower than the resonant frequency at which the disk drive read rate and write rate are within a predetermined amount of their level when the disk drive is not vibrating.

In some embodiments, during operation of fan 104, fan controller 102 controls the operation of fan 104 based on performance parameters of computer system 100 including, for example, in some embodiments, the temperature of a processor in computer system 100 that is being cooled by fan 104. As fan controller 102 controls the speed of fan 104, fan controller 102 sends a signal to critical-vibration-frequency library 106 to determine if the speed setting that fan controller 102 is going to set for fan 104 is in a keep-out zone. If fan controller 102 receives a signal that the speed setting is in a keep-out zone then, based on the available thermal margin, fan controller 102 will control fan 104 to operate at a speed setting just above or just below the keep-out zone. In some embodiments, if fan controller 102 desires to control the speed of fan 104 to pass through a keep-out zone, fan controller 102 will control fan 104 to pass through the keep-out zone in a predetermined manner. In some embodiments, the predetermined manner can include but is not limited to controlling fan 104 to pass through the keep-out zone as rapidly as possible, while in other embodiments, fan 104 is controlled to pass through the keep-out zone in a predetermined time based on information related to the behavior of computer system 100 in the keep-out zone and/or at the critical frequency. For example, the rate at which the speed of fan 104 is controlled to pass through a keep-out zone related to a disk drive performance can be related to the degradation of the read rate and write rate of the disk drive at the critical frequency.

In some embodiments, the device that generates vibrations can be a device other than a fan and can include but is not limited to a disk drive; a mechanical pump, such as a liquid coolant pump; or any other device that can generate vibrations over a frequency range in a computer system.

Figure 2:
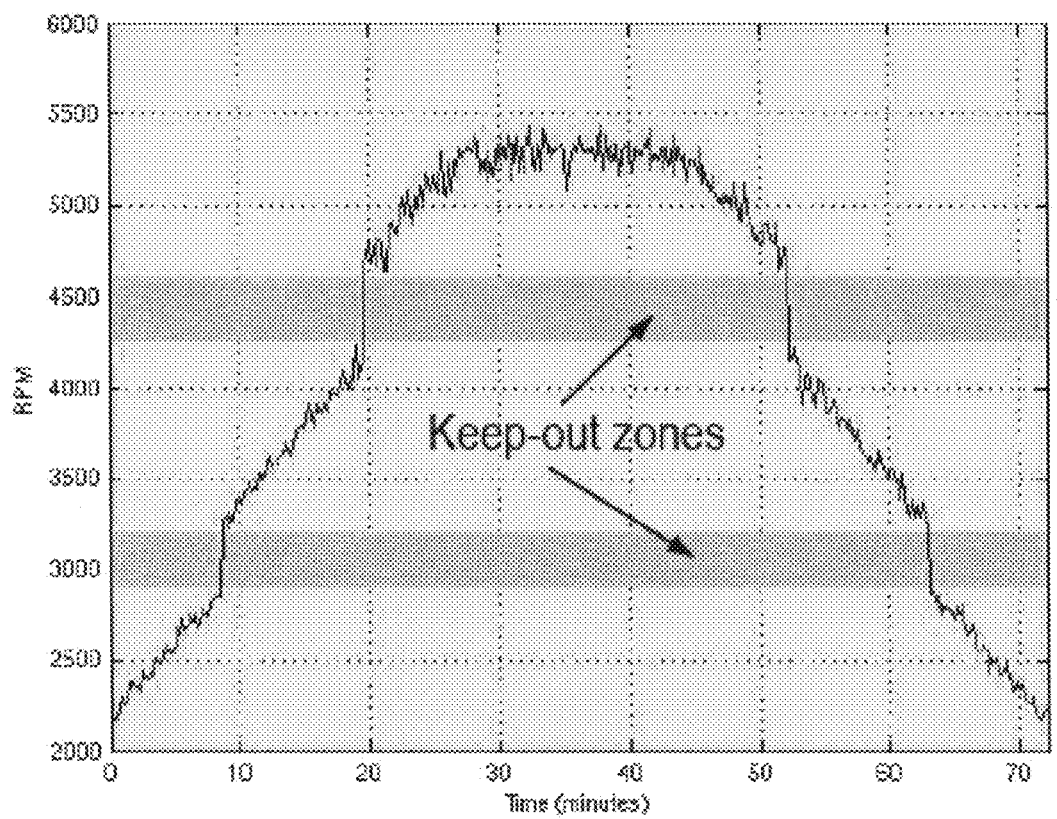
FIG. 2 presents a graph of fan sweep showing fan RPMs vs. time illustrating keep-out zones in accordance with some embodiments of the present invention.

FIG. 2 presents a graph of fan sweep showing fan speed in RPMs vs. time illustrating keep-out zones in accordance with some embodiments of the present invention. In FIG. 2 a computer system fan is controlled to sweep in RPMs from below 2500 RPMs to above 5000 RPMs and back to below 2500 RPM through 2 keep-out zones. As depicted in FIG. 2, the fan speed is controlled to pass through the keep-out zones at a sweep rate that greatly exceeds the sweep rate outside of the keep-out zones in order to limit the duration of vibrations generated by the fan at the critical frequency and in the keep-out zones.

Figure 3:
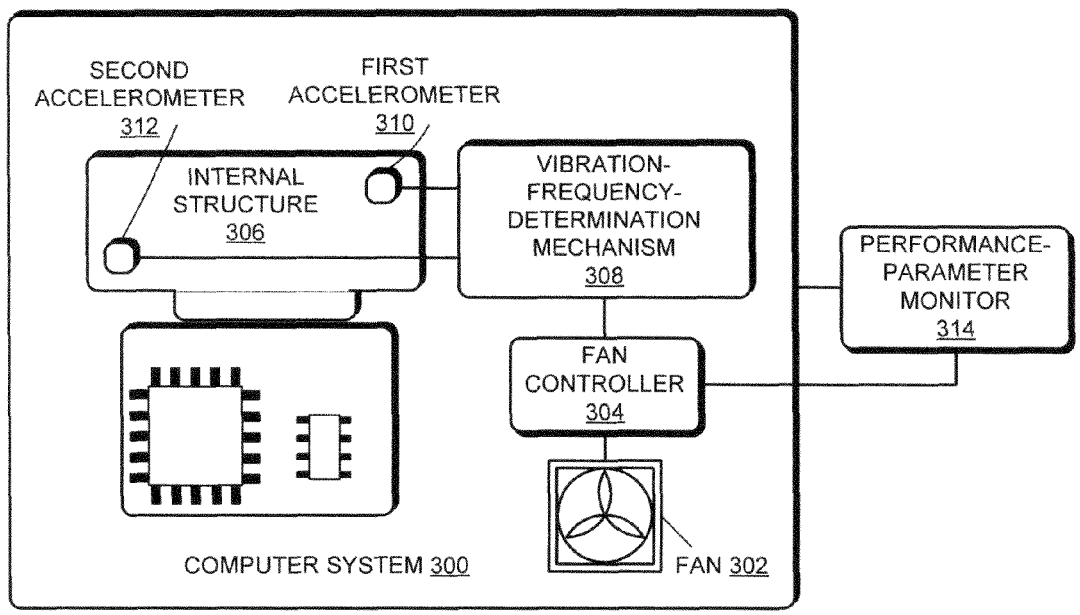
FIG. 3 represents a system that controls a device that generates vibrations in a computer system in accordance with some embodiments of the present invention.

FIG. 3 represents a system that controls a device that generates vibrations in a computer system in accordance with some embodiments of the present invention. Computer system 300 includes fan 302, fan controller 304, internal structure 306, and vibration-frequency-determination mechanism 308. First accelerometer 310 and second accelerometer 312 are mounted to internal structure 306 and coupled to vibration-frequency-determination mechanism 308. Performance parameter monitor 314 is coupled to computer system 300 and fan controller 304. Fan controller 304 is coupled to fan 302, vibration frequency control mechanism 308, and performance parameter monitor 314.

Computer system 300 can include but is not limited to a server, server blade, a datacenter server, an enterprise computer, a field-replaceable unit that includes a processor, or any other computation system that includes one or more processors and one or more cores in each processor.

Fan 302 can include any type of fan that can be used to cool computer system 300 or any computer system component inside computer system 300. Fan 302 can be implemented in any technology. In some embodiments, fan 302 generates vibrations related to the speed of fan 302.

Fan controller 304 can be any controller that can control the speed of fan 302. Fan controller 304 can be implemented in any combination of hardware and software. In some embodiments, fan controller 304 operates on a processor in computer system 300. In some embodiments, fan controller 304 operates on one or more service processors. In still other embodiments, fan controller 304 operates on a processor outside of computer system 300.

Internal structure 306 can be any internal structure of computer system 300. First accelerometer 310 and second accelerometer 312 are coupled to internal structure 306 and measure acceleration of internal structure 306 at their respective locations and transmit signals to vibration-frequency-determination mechanism 308 related to the acceleration measured by each accelerometer. First accelerometer 310 and second accelerometer 312 can be implemented in any technology and can include but are not limited to integrated electronics piezoelectric accelerometers, micro-electromechanical (MEMS) accelerometers, mechanical or optical accelerometers, remote sensing devices, or any other device or system that can measure acceleration at a specified location.

Vibration-frequency-determination mechanism 308 receives signals from first accelerometer 310 and second accelerometer 312 and determines the vibration frequency of internal structure 306. Vibration-frequency-determination mechanism 308 can be implemented in any combination of hardware and software. In some embodiments, vibration-frequency-determination mechanism 308 operates on a processor in computer system 100. In other embodiments, vibration-frequency-determination mechanism 308 operates on one or more service processors. In other embodiments, vibration-frequency-determination mechanism 308 operates on a separate computer system. In some embodiments, vibration-frequency-determination mechanism 308 is integrated into fan controller 304.

It is noted that in some embodiments, more or fewer than two accelerometers are used. In some embodiments, the number of accelerometers coupled to internal structure 306 is based on the location and type of vibrations to be detected. In some embodiments, four 3-axis accelerometers that measure acceleration in three orthogonal directions are coupled to internal structure 306 on the vertices of a known tetrahedron so that the spatial relationship between the locations of the accelerometers is known, and such that all four of the accelerometers are not in the same plane and no three of the accelerometers form a straight line. In some embodiments, in which vibrations in a predetermined plane are to be measured, three 2-axis accelerometers are used and their axes are placed parallel to the vibration plane to be measured. In some embodiments, accelerometers are coupled to other computer system components or other locations in computer system 300 to measure vibrations of the other computer system components or locations in computer system 300.

Performance-parameter monitor 314 can be any device that can monitor performance parameters of computer system 300, including but not limited to a read rate and write rate of a hard disk drive (HDD) in computer system 300 or any other performance parameters as set forth in U.S. Pat. No. 7,020,802. Performance-parameter monitor 314 can be implemented in any combination of hardware and software. In some embodiments, performance-parameter monitor 314 operates on computer system 300. In other embodiments, performance-parameter monitor 314 operates on one or more service processors. In still other embodiments, performance-parameter monitor 314 is located inside computer system 300. In yet other embodiments, performance-parameter monitor 314 operates on a separate computer system. In some embodiments, performance-parameter monitor 314 is integrated into fan controller 304.

Some embodiments of the present invention operate as follows. Fan controller 304 controls the speed of fan 302. As the temperature in computer system 300 varies, fan controller 304 controls the speed of fan 302 to increase or decrease based on the temperature and thermal budget of computer system 300. During operation of computer system 300 first accelerometer 310 and second accelerometer 312 send signals to vibration-frequency-determination mechanism 308 related to the sensed acceleration. Vibration-frequency-determination mechanism 308 then determines the vibration frequency of internal structure 306 based on the signals received from first accelerometer 310 and second accelerometer 312. Vibration-frequency-determination mechanism 308 then sends a signal to fan controller 304 related to the determined vibration frequency.

Performance-parameter monitor 314 monitors performance parameters of computer system 300 and sends a signal to fan controller 304 related to the monitored performance parameters. In some embodiments, performance-parameter monitor 314 monitors the read rate and write rate of an HDD in computer system 300 and sends a signal related to the monitored read rate and write rate to fan controller 304.

In some embodiments, fan controller 304 determines if the vibration frequency determined by vibration-frequency-determination mechanism 308 is at or near a critical vibration frequency based on the monitored read rate and write rate for the HDD monitored by performance parameter 314. In some embodiments, fan controller 304 additionally uses the vibration frequency determined by vibration-frequency-determination mechanism 308 to determine if the determined vibration frequency is at or near a critical vibration frequency or keep-out zone in a critical-vibration-frequency library in fan controller 304.

In some embodiments, if fan controller 304 determines that the determined frequency from vibration-frequency-determination mechanism 308 is at or near a critical frequency, then fan controller 304 generates a keep-out zone based on information from performance-parameter monitor 314 and vibration-frequency-determination mechanism 308. Then, fan controller 304, taking into account the thermal budget of computer system 300, controls the speed of fan 302 to a fan speed above or below the generated keep-out zone. For example, if fan controller 304 can lower the speed of fan 302 below the keep-out zone and preserve thermal budget, it preferentially does so to save additional energy. If doing so would shrink the thermal budget below a predetermined threshold, then the fan controller 304 will increase the speed of fan 302 above the keep-out zone.

In some embodiments, the keep-out zone is generated by fan controller 304 based on the relationship between the vibration frequency determined by vibration-frequency-determination mechanism 308 and the read rate and write rate monitored by performance-parameter monitor 314 for the HDD in computer system 300 over time. In some embodiments, fan controller 304 implements a multiple input, multiple output (MIMO) controller that generates a keep-out zone based on inputs from vibration-frequency-determination mechanism 308 and performance-parameter monitor 314.

It is noted that first accelerometer 310 and second accelerometer 312 can be coupled to any other internal structure or computer system component or device. In some embodiments, the choice of where to couple first accelerometer 310 and second accelerometer 312 is based on factors including but not limited to one or more of the following: the location of the source of the vibrations; and the location of one or more computer system components affected by the vibrations, and the degree to which vibrations impact their performance. In some embodiments, more than one set of accelerometers is placed in computer system 300.

Figure 4:
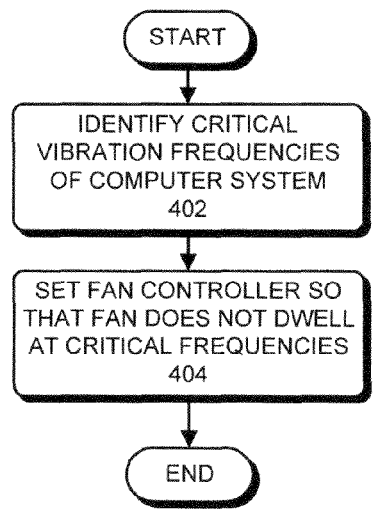
FIG. 4 presents a flowchart illustrating a process for controlling a device that generates vibrations in a computer system in accordance with some embodiments of the present invention.

FIG. 4 presents a flowchart illustrating a process for controlling a device that generates vibrations in a computer system in accordance with some embodiments of the present invention. First, the critical vibration frequencies of the computer system are identified (step 402). In some embodiments, the critical vibration frequencies are identified using any techniques to identify critical vibration frequencies of a computer system or computer system components in the computer system, and can include but are not limited to structural resonances and other critical frequencies of the computer system and/or computer system components. Then, the fan controller is set so that the fan does not dwell at the critical frequencies (step 404). In some embodiments, setting the fan controller so that the fan does not dwell at the critical frequencies includes but is not limited to generating keep-out zones based on the critical frequencies.

The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. A method for controlling a device that generates vibrations in a computer system, the method comprising:
    determining a critical vibration frequency for the computer system;
    generating a keep-out zone based on the critical vibration frequency, wherein the keep-out zone specifies a continuous range of frequencies to be avoided, and wherein a width for the continuous range of frequencies is determined based on measurements related to determining the critical vibration frequency; and
    controlling the device based on the keep-out zone to reduce vibrations generated by the device in the keep-out zone, wherein controlling the device based on the keep-out zones comprises causing the device to pass through the keep-out zone in a predetermined manner based on the behavior of the computer system as the device passes through the keep-out zone.

2. The method of claim 1, wherein determining the critical vibration frequency includes monitoring a computer system component performance parameter while the computer system is vibrating in a frequency range.

3. The method of claim 2, wherein the computer system is vibrated in the frequency range using a vibration-generation mechanism located inside the computer system.

4. The method of claim 2, wherein the width for the continuous range of frequencies is determined based on measurements of the computer system component performance parameter.

5. The method of claim 2, wherein the width for the continuous range of frequencies is determined based on vibration frequencies higher and lower than the critical vibration frequency at which the computer system component performance parameter is within a predetermined amount of a level for the computer system component performance parameter when the computer system is not vibrating.

6. The method of claim 1, wherein:
    determining the critical vibration frequency for the computer system includes determining a critical vibration frequency for each computer system component in a set of computer system components in the computer system.

7. The method of claim 6, further comprising:
    generating a library of critical vibration frequencies for the computer system based on the critical vibration frequency for each computer system component in the set of computer system components, wherein generating the keep-out zone includes generating the keep-out zone based on critical vibration frequencies in the library of critical vibration frequencies.

8. The method of claim 1, wherein determining the critical vibration frequency includes determining the critical vibration frequency based on monitoring a performance parameter of the computer system during operation of the computer system and monitoring a vibration frequency of the computer system during operation of the computer system.

9. The method of claim 1, wherein the device includes at least one of:
    a fan; and
    a disk drive.

10. A non-transitory computer-readable storage medium storing instructions that when executed by a computer cause the computer to perform a method for controlling a device that generates vibrations in a computer system, the method comprising:
    determining a critical vibration frequency for the computer system;
    generating a keep-out zone based on the critical vibration frequency, wherein the keep-out zone specifies a continuous range of frequencies to be avoided, and wherein a width for the continuous range of frequencies is determined based on measurements related to determining the critical vibration frequency; and controlling the device based on the keep-out zone to reduce vibrations generated by the device in the keep-out zone, wherein controlling the device based on the keep-out zones comprises causing the device to pass through the keep-out zone in a predetermined manner based on the behavior of the computer system as the device passes through the keep-out zone.

11. The computer-readable storage medium of claim 10, wherein determining the critical vibration frequency includes monitoring a computer system component performance parameter while the computer system is vibrating in a frequency range.

12. The computer-readable storage medium of claim 11, wherein the computer system is vibrated in the frequency range using a vibration-generation mechanism located inside the computer system.

13. The computer-readable storage medium of claim 10, wherein:
determining the critical vibration frequency for the computer system includes determining a critical vibration frequency for each computer system component in a set of computer system components in the computer system.

14. The computer-readable storage medium of claim 13, further comprising:
generating a library of critical vibration frequencies for the computer system based on the critical vibration frequency for each computer system component in the set of computer system components, wherein generating the keep-out zone includes generating the keep-out zone based on critical vibration frequencies in the library of critical vibration frequencies.

15. The computer-readable storage medium of claim 10, wherein determining the critical vibration frequency includes determining the critical vibration frequency based on monitoring a performance parameter of the computer system during operation of the computer system.

16. The computer-readable storage medium of claim 10, wherein determining the critical vibration frequency includes determining the critical vibration frequency based on monitoring a performance parameter of the computer system during operation of the computer system and monitoring a vibration frequency of the computer system during operation of the computer system.

17. An apparatus that controls a device that generates vibrations in a computer system, the apparatus comprising:
a determining mechanism configured to determine a critical vibration frequency for the computer system;

a generating mechanism configured to generate a keep-out zone based on the critical vibration frequency, wherein the keep-out zone specifies a continuous range of frequencies to be avoided, and wherein a width for the continuous range of frequencies is determined based on measurements related to determining the critical vibration frequency; and a controlling mechanism configured to control the device based on the keep-out zone to reduce vibrations generated by the device in the keep-out zone, wherein controlling the device based on the keep-out zones comprises causing the device to pass through the keep-out zone in a predetermined manner based on the behavior of the computer system as the device passes through the keep-out zone.

18. The apparatus of claim 17, further comprising:
a library of critical vibration frequencies for the computer system, wherein the library of critical vibration frequencies is based on the critical vibration frequency for each computer system component in a set of computer system components; and wherein the generating mechanism generates the keep-out zone based on critical vibration frequencies in the library of critical vibration frequencies.

19. The apparatus of claim 17,
wherein the determining mechanism includes a mechanism configured to determine the critical vibration frequency based on monitoring a performance parameter of the computer system during operation of the computer system, and monitoring a vibration frequency of the computer system.

* * * * *